US006993971B2

(12) United States Patent
Bossi et al.

(10) Patent No.: US 6,993,971 B2
(45) Date of Patent: Feb. 7, 2006

(54) ULTRASONIC INSPECTION DEVICE FOR INSPECTING COMPONENTS AT PRESET ANGLES

(75) Inventors: Richard H. Bossi, Renton, WA (US); Martin Freet, Federal Way, WA (US); Gary E. Georgeson, Federal Way, WA (US); Stanley W. Richardson, Bothell, WA (US)

(73) Assignee: The Boeing Company, Chicago, IL (US)

( * ) Notice: Subject to any disclaimer, the term of this patent is extended or adjusted under 35 U.S.C. 154(b) by 3 days.

(21) Appl. No.: 10/734,452

(22) Filed: Dec. 12, 2003

(65) Prior Publication Data

US 2005/0126294 A1 Jun. 16, 2005

(51) Int. Cl.
*G01N 29/24* (2006.01)
*G01N 29/26* (2006.01)

(52) U.S. Cl. .......................................... 73/620; 73/633
(58) Field of Classification Search .................. 73/620, 73/623, 629, 633, 640, 643
See application file for complete search history.

(56) References Cited

U.S. PATENT DOCUMENTS

| | | | | |
|---|---|---|---|---|
| 2,459,162 A | * | 1/1949 | Hayes | 181/125 |
| 3,121,324 A | * | 2/1964 | Cowan | 73/618 |
| 3,791,201 A | * | 2/1974 | Dory | 73/640 |
| 4,117,733 A | | 10/1978 | Gugel | |
| 4,185,501 A | | 1/1980 | Proudian et al. | |
| 4,200,885 A | * | 4/1980 | Hofstein | 348/163 |
| 4,361,044 A | * | 11/1982 | Kupperman et al. | 73/623 |
| 4,466,286 A | | 8/1984 | Berbeé et al. | |
| 4,526,037 A | | 7/1985 | Wentzell et al. | |
| 4,541,434 A | * | 9/1985 | Okado | 600/446 |
| 4,612,808 A | | 9/1986 | McKirdy et al. | |
| 4,807,476 A | | 2/1989 | Cook et al. | |
| 4,848,159 A | * | 7/1989 | Kennedy et al. | 73/641 |
| 4,862,748 A | * | 9/1989 | Woodmansee | 73/641 |
| 4,980,872 A | | 12/1990 | Oler et al. | |
| 5,203,869 A | * | 4/1993 | Bashyam | 73/640 |
| 2002/0006079 A1 | | 1/2002 | Saito et al. | |
| 2002/0017140 A1 | | 2/2002 | Georgeson et al. | |

FOREIGN PATENT DOCUMENTS

EP 1 214 909 6/2002

\* cited by examiner

Primary Examiner—Hezron Williams
Assistant Examiner—Rose M. Miller
(74) Attorney, Agent, or Firm—Alston & Bird LLP

(57) ABSTRACT

There is provided an ultrasonic inspection device that provides a locking mechanism for inspecting components at preset angles. The inspection device can inspect a component along an arc by inspecting the component at each preset angle, which provides complete and repeatable inspection results. The inspection device comprises a housing with a channel for the passage of an ultrasonic signal and an ultrasonic transducer to transmit and receive the ultrasonic signals. The housing also includes a rotating reflector to reflect the ultrasonic signal. Using a handle on the housing rotatably attached to the rotating reflector, a technician can rotatably position and lock the rotating reflector at a preset angle. The rotating reflector can be rotatably locked by a spring-loaded ball that is selectively received in detents defined by the rotating reflector or handle.

22 Claims, 7 Drawing Sheets

ULTRASONIC INSPECTION DEVICE FOR INSPECTING COMPONENTS AT PRESET ANGLES

FEDERALLY SPONSORED RESEARCH OR DEVELOPMENT

This invention was made with government support under Contract No. F33615-98-3-5103 awarded by the Department of the Air Force. The government may have certain rights in this invention.

FIELD OF THE INVENTION

The present invention relates generally to ultrasonic inspection devices. More particularly the invention relates to an ultrasonic inspection device that inspects a component at preset angles.

BACKGROUND OF THE INVENTION

Non-destructive inspection of components involves thoroughly examining a component without harming the component or requiring significant disassembly of the component. Non-destructive inspection is advantageous for many applications in which a thorough inspection of the exterior and/or interior of a component is required. Internal defects of a component, such as delamination of composites or cracks and voids in weld joints, may be inspected with non-destructive sensors such as ultrasonic transducers. Ultrasonic transducers transmit ultrasonic signals into a component and receive echoes generated when the signal reflects off internal defects in the component.

Components having curved or non-planar surfaces often require ultrasonic inspection at multiple angles so that the ultrasonic signal is transmitted into the component such that the echoed signal reflects back to the inspection device. An example of such a component is a 90 degree weld joint. Inspection of the joint at a single angle may cause the signals reflected off any defects that are not generally perpendicular to the inspection signal to echo in a direction away from the inspection device such that the echo is not received by the inspection device and the defect is not fully detected. The joint is preferably inspected at multiple angles so that the echoed signals reflecting off any defects in the joint are received by the ultrasonic inspection device. Hand-held devices are commonly used to inspect curved or non-planar components, and some devices are also manually advanced along the component by a technician while the technician monitors the outputs of the ultrasonic test equipment.

Manual inspection devices may include features to assist a technician performing an ultrasonic inspection. U.S. Pat. No. 4,807,476 to Cook et al. (the "'476 patent") discloses an ultrasonic shoe having a single ultrasonic transducer that utilizes a double reflector system to inspect a radius along a 90 degree arc. The ultrasonic shoe has an external handle that rotates one mirror relative to a stationary mirror to inspect a radius along a 90 degree arc. Thus, a transducer in a fixed orientation, relative to the component being inspected, can inspect the part along a 90 degree arc. To inspect the part, the technician preferably positions the shoe proximate the radius to be inspected and turns the mirror to a certain angular orientation. The technician then advances the shoe along the length of the radius being inspected. The technician then turns the handle a certain angle and repeats the advancement of the shoe. This procedure may be iterated until the radius has been sufficiently inspected. Alternatively, the technician may advance the shoe while repeatedly "sweeping" the rotatable mirror between the 0 degree and 90 degree positions.

The efficacy of the ultrasonic shoe of the '476 patent may be limited because the technician may unintentionally fail to inspect portions of a radius or may repeatedly inspect portions of the radius because of the subjective nature of orienting the handle. The technician can reasonably locate the 0 and 90 degree settings of the handle, and thus inspect the two extremes of the radius, but inspecting the intermediate portions of the radius is less repeatable or efficient. Furthermore, the "sweeping" method may not produce reliable results because of the subjective nature of "sweeping" the rotatable mirror.

Therefore, a need exists for an ultrasonic inspection device that inspects a component to provide complete and repeatable inspection results while minimizing the number of iterations required to fully inspect the component.

BRIEF SUMMARY OF THE INVENTION

The invention addresses the above needs and achieves other advantages by providing an ultrasonic inspection device that incorporates a locking mechanism to lock a rotating reflector at preset angles which, in turn, controls the angle at which the ultrasonic signals are introduced into a component under inspection. The inspection device includes a housing with a channel for the passage of an ultrasonic signal. A transducer that transmits and receives the ultrasonic signal is in communication with the housing. A rotating reflector, which is generally attached to a handle, directly or indirectly reflects the ultrasonic signal to and from the transducer. The locking mechanism locks the rotating reflector at two or more preset angles such that a technician using the inspection device can produce complete and repeatable inspection results with minimal inspection iterations.

The locking mechanism of further embodiments of the invention includes detents in the handle or the rotating reflector and a spring-loaded ball in the housing. The angular position of the detents correspond with the preset angles and the spring-loaded ball rotatably locks the handle or rotating reflector at a preset angle selected by a technician. The preset angles may be separated by angles such as 22.5 degrees, 30 degrees, or 45 degrees.

A method of inspecting a component is also provided by the present invention. An ultrasonic inspection device is positioned proximate the component to be inspected such that an aperture defined by the ultrasonic inspection device opens toward the component. A rotating reflector is positioned at a preset angle, and the ultrasonic signal is transmitted through the ultrasonic inspection device such that the ultrasonic signal reflects from the rotating reflector toward a portion of the component. The rotating reflector is then moved to another preset angle to facilitate inspection of another portion of the composite.

The method may further include the step of rotating a handle, which is rotatably attached to the rotating reflector, prior to transmitting additional ultrasonic signals. Furthermore, the method may include rotating the handle to a third preset angle and to a plurality of preset angles and transmitting additional ultrasonic signals with the handle at each preset angle to inspect a first portion of the component. In addition, the method may include advancing the ultrasonic inspection device along the length of the component to inspect a second portion of the component at the preset angles. Alternatively, the method may include advancing the ultrasonic inspection device along the length of the component to inspect lengthwise portions of the component. The rotating reflector may be moved to another preset angle and the ultrasonic inspection device again advanced along the length of the component to inspect another lengthwise portion of the component. This procedure may be repeated until all the lengthwise portions of the component have been inspected.

The inspection device and method therefore provide complete and repeatable inspection results while minimizing the number of iterations required to fully inspect the component.

BRIEF DESCRIPTION OF THE SEVERAL VIEWS OF THE DRAWINGS

Figure 1:
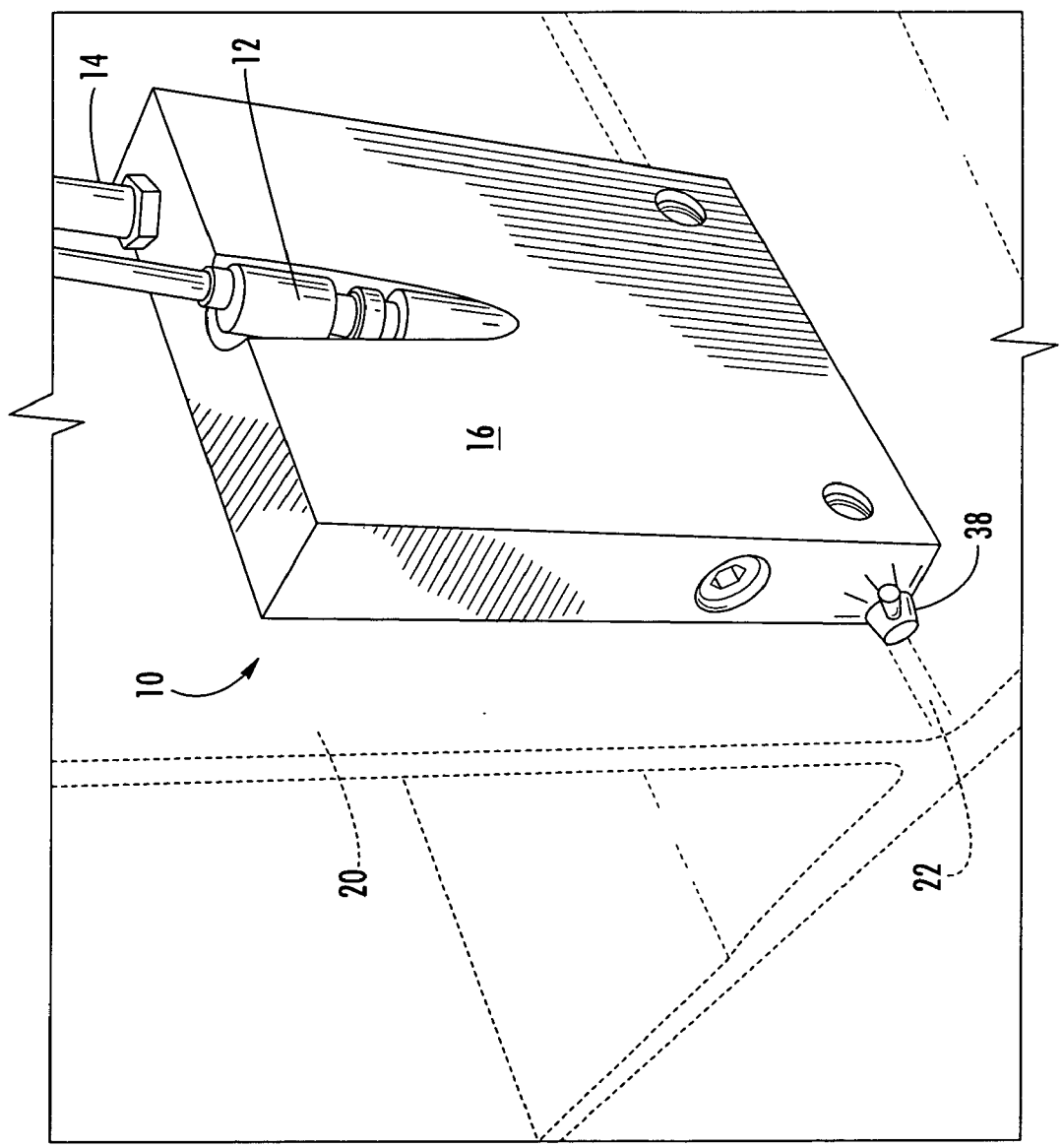
Figure 2:
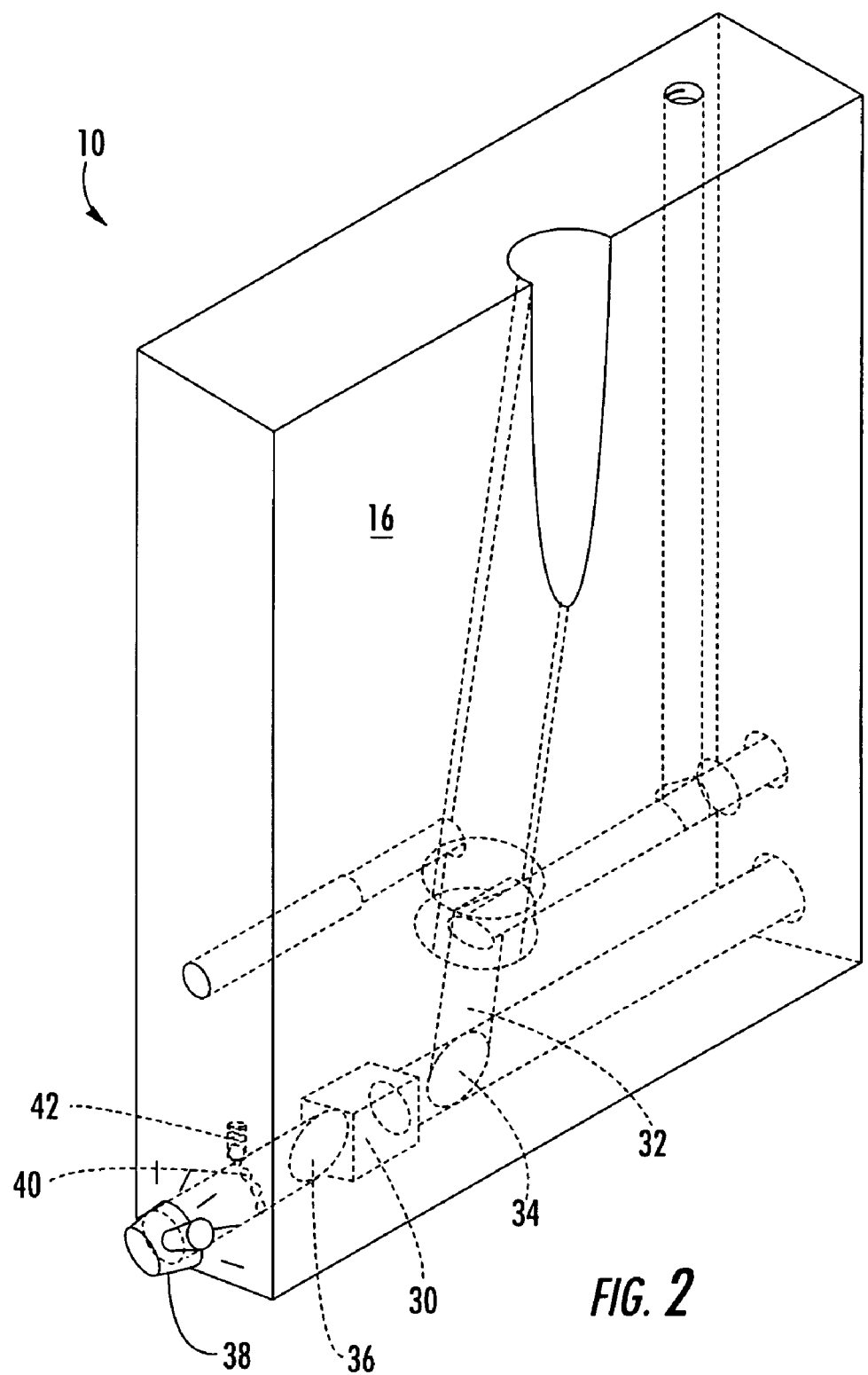
Figure 3:
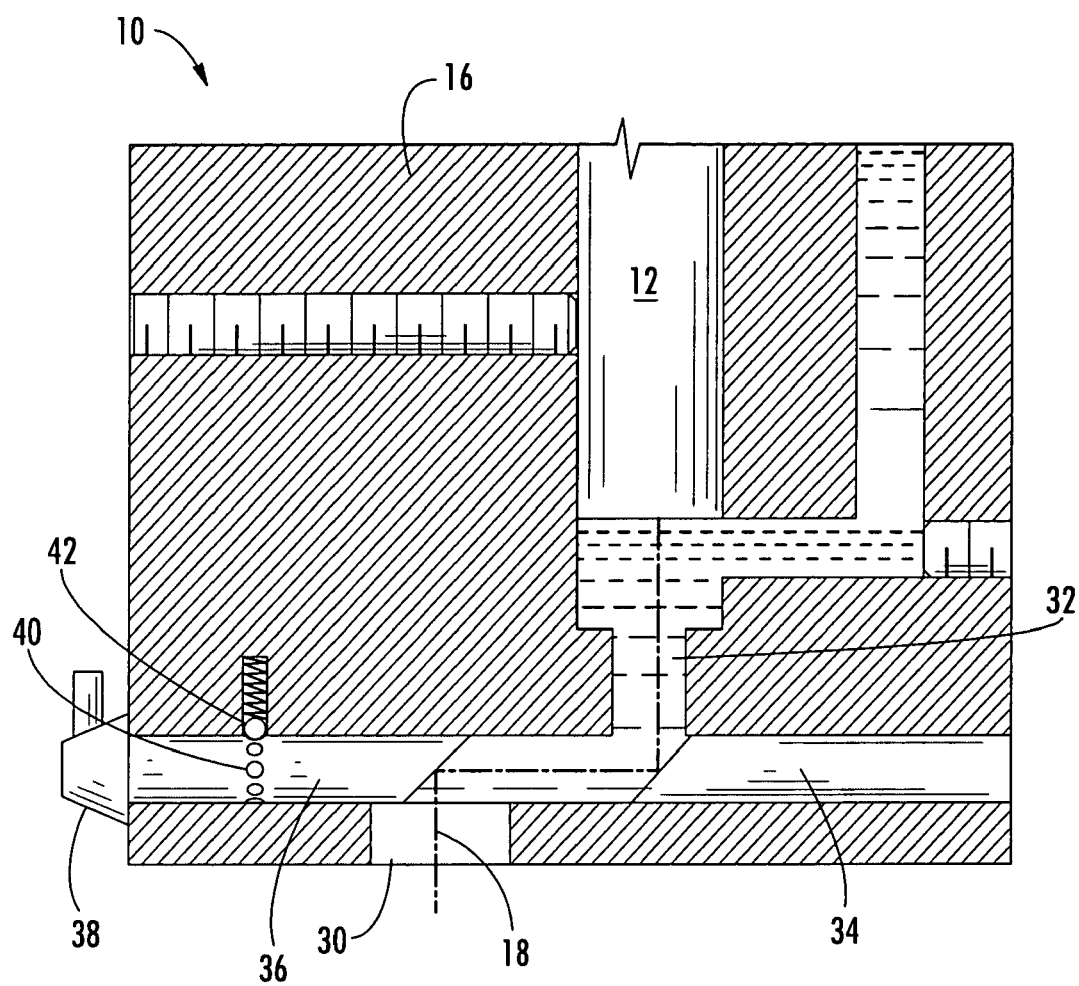
Figure 4:
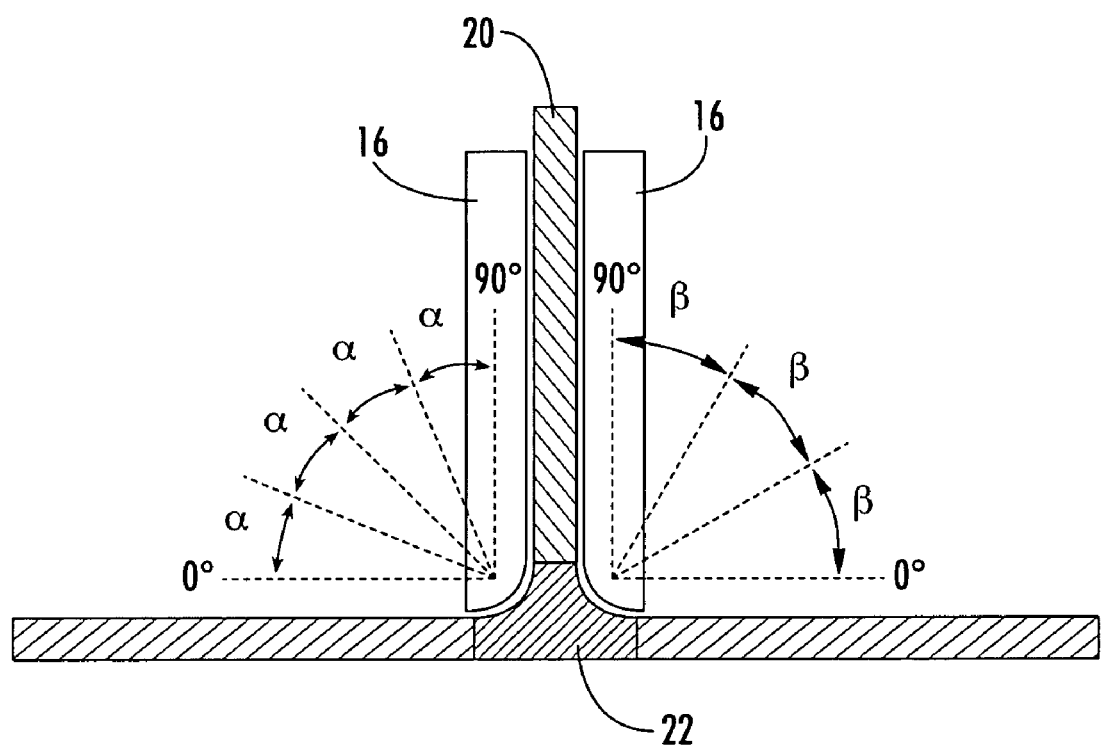
Figure 5:
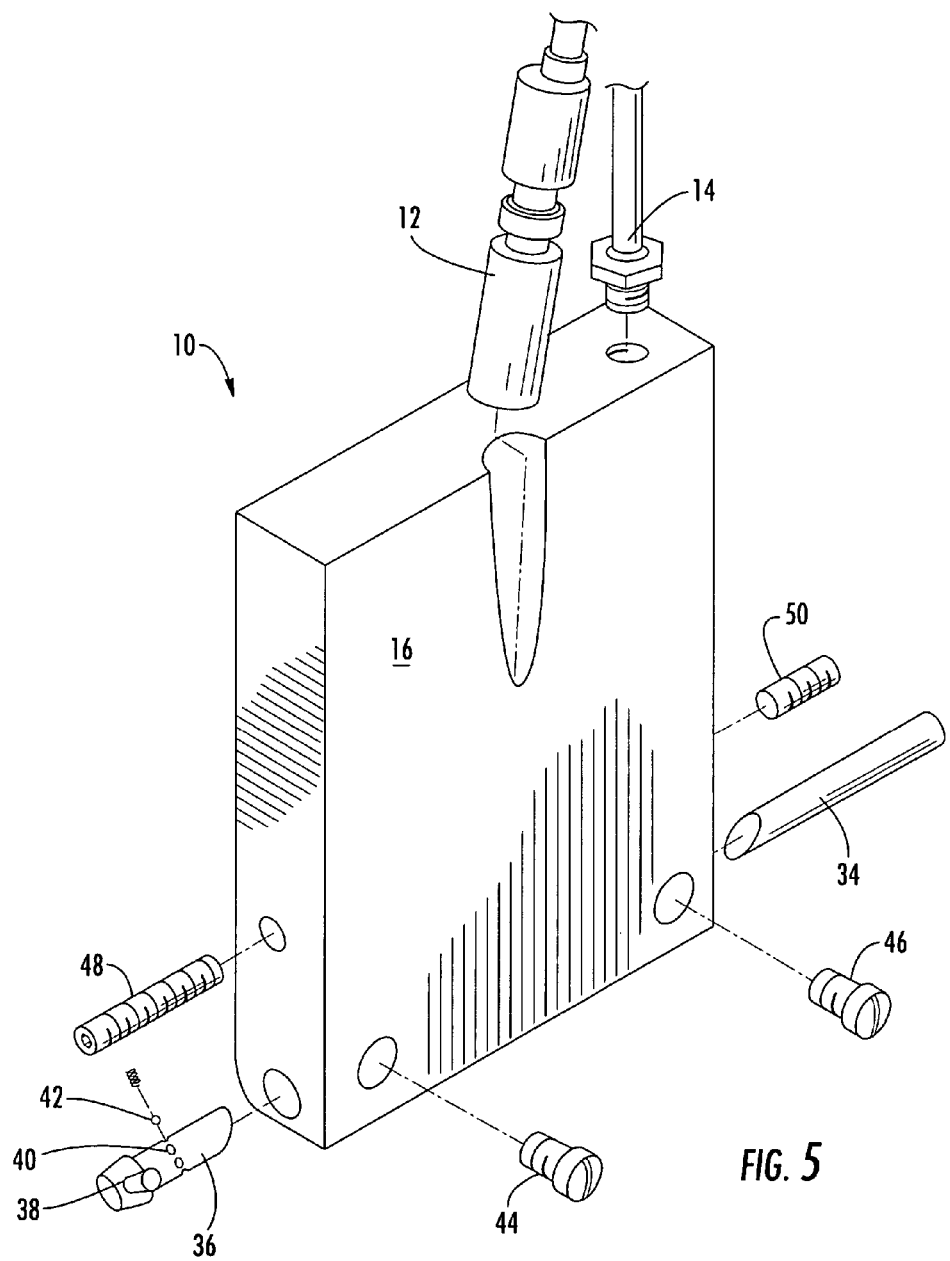
Figure 6:
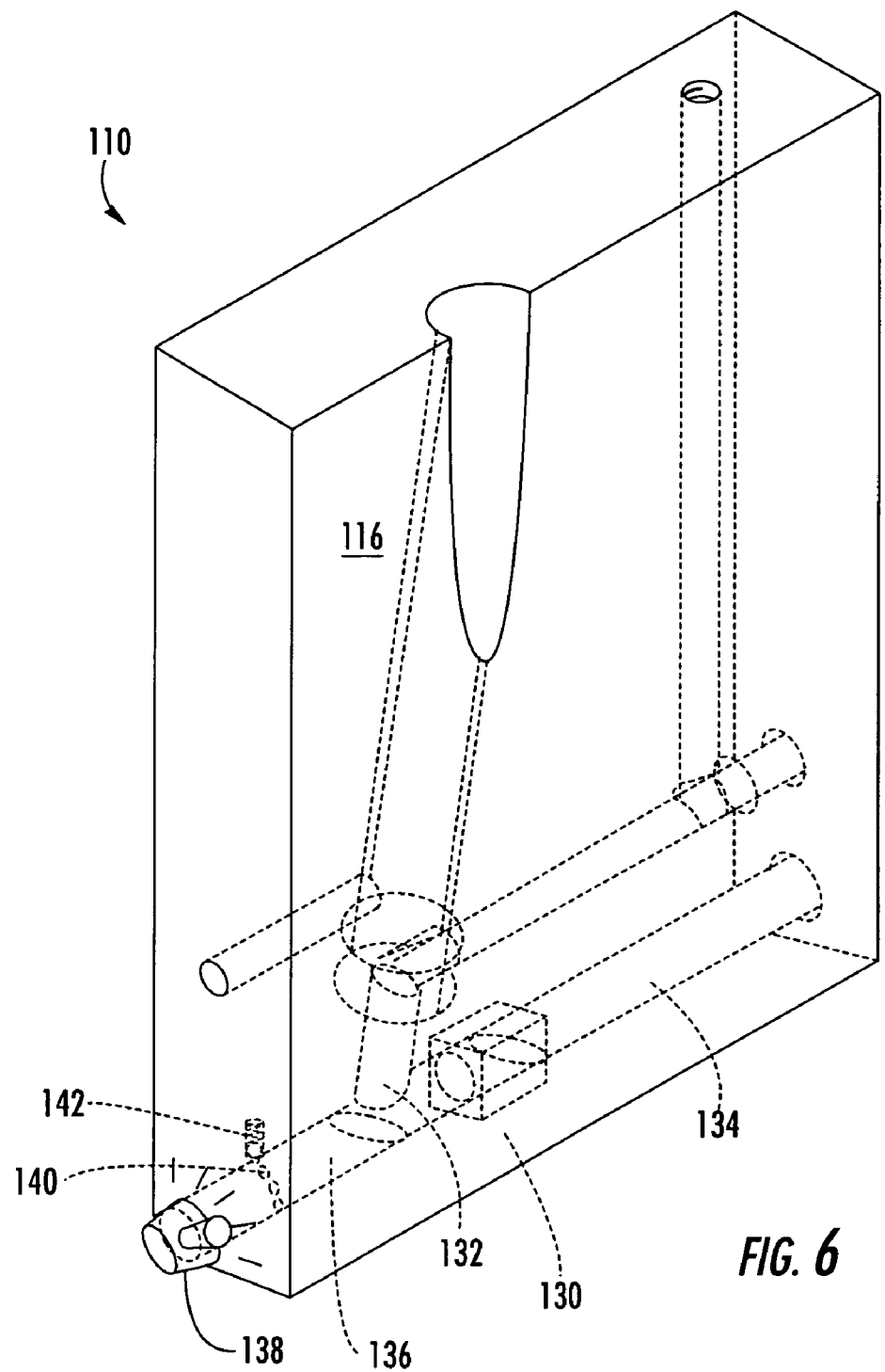
Figure 7:
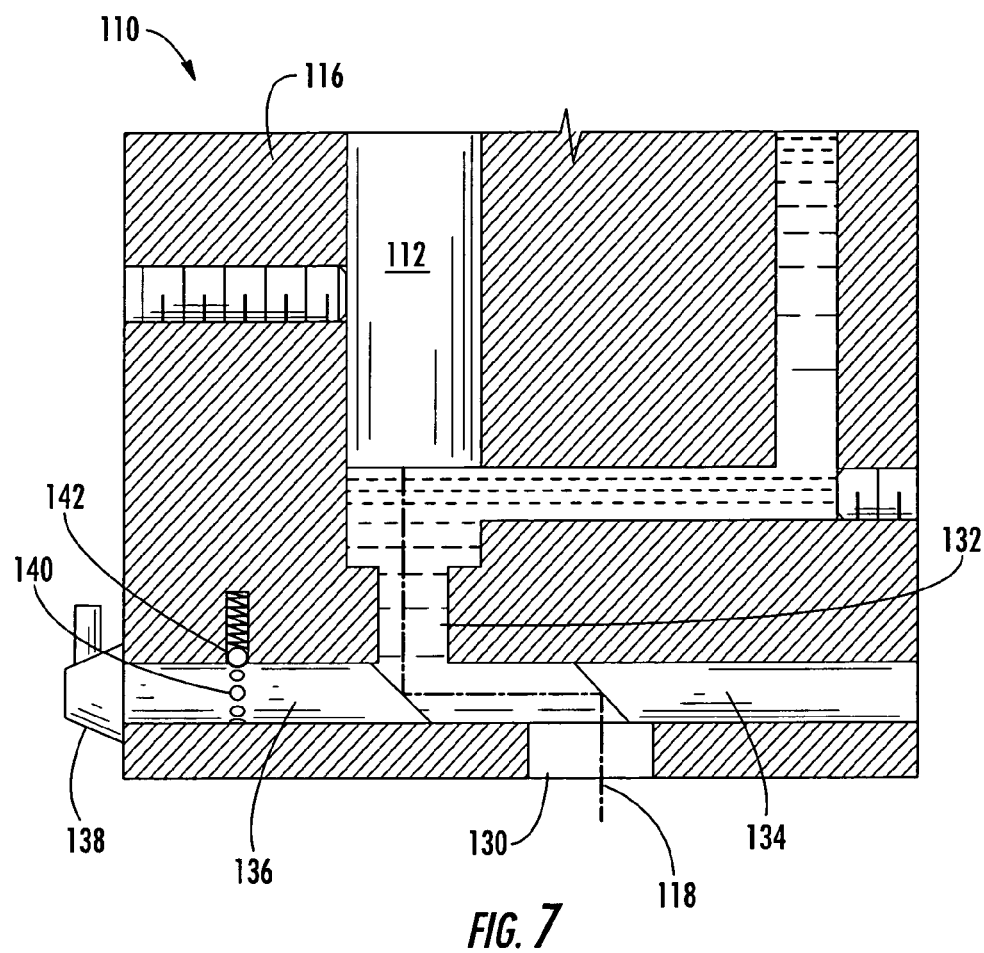

Having thus described the invention in general terms, reference will now be made to the accompanying drawings, which are not necessarily drawn to scale, and wherein:

FIG. 1 is an environmental view of an ultrasonic inspection device in accordance with one embodiment of the present invention, illustrating the inspection device proximate a T-joint of a component;

FIG. 2 is a perspective view of the ultrasonic inspection device of FIG. 1, illustrating the channel and reflectors;

FIG. 3 is a schematic, cross-sectional view of the ultrasonic inspection device of FIG. 1, illustrating the path of the ultrasonic signal;

FIG. 4 is a diagrammatic view showing a 90 degree arc illustrating preset angles separated by 22.5 degrees on the left and by 30 degrees on the right;

FIG. 5 is an exploded, perspective view of the ultrasonic inspection device of FIG. 1, illustrating the assembly of the ultrasonic inspection device;

FIG. 6 is a perspective view of the ultrasonic inspection device of a second embodiment of the invention, illustrating the channel and reflectors; and FIG. 7 is a schematic, cross-sectional view of the ultrasonic inspection device of FIG. 6, illustrating the path of the ultrasonic signal.

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

With reference to FIGS. 1–5, an ultrasonic inspection device 10 in accordance with one embodiment of the invention is illustrated. The inspection device 10 of the present invention includes an ultrasonic transducer 12 in communication with the housing of the inspection device for transmitting and receiving an ultrasonic signal therethrough to indicate the presence of internal defects in an inspected component. The ultrasonic transducer 12 of the illustrated embodiment includes a piezo-electric transducer connected to a portable pulse/receiver ultrasonic test equipment. Alternative transducers 12 may be used in further embodiments of the inspection device 10. The inspection device 10 also includes a water source 14 attached to the housing 16 of the inspection device. The water provided by the water source 14 serves as a couplant through which the ultrasonic signal 18 may propogate, as illustrated in FIG. 3. Alternative couplants, such as gel couplants, may also be used with the present invention. The '476 patent discussed above, which is assigned to the present assignee, discloses an ultrasonic inspection device comprising these and other components. The disclosure of the '476 patent is incorporated herein.

FIG. 1 illustrates the inspection device 10 positioned proximate the component 20 to be inspected. Components 20 inspected by the inspection device 10 may consist of materials that include but are not limited to composites, metals, and polymers. The illustrated component 20 comprises a composite defining a T-joint, such that the joint 22 is a composite radii that requires inspection for internal defects. Alternatively, the joint 22 to be inspected may be a pi joint defined by two receiving tabs or portions of a first component into which a second component is joined. The joint 22 may further define a weld joint or any other curved feature of the component 20 in still further embodiments of the present invention. The inspection device 10 of the illustrated embodiment is structured to inspect curved surfaces along a 90 degree arc such that the ultrasonic signal remains perpendicular to the inspected surface throughout the inspection process. However, inspection devices of further embodiments may be structured to inspect components of any shape, such as flat or polygonal components or components having arcs greater or less than 90 degrees, to list non-limiting examples. The corner of the housing 16 that is proximate the joint 22 to be inspected is preferably radiused to more closely correspond with the curved surfaces that are inspected.

To inspect the joint 22 of FIG. 1, the inspection device 10 is positioned proximate the component 20 such that an aperture 30 of the housing 16 opens toward the joint. The aperture 30 is preferably located in the radiused corner of the housing 16. The aperture 30 is illustrated in FIGS. 2 and 3 and is an arcuate opening defined in the housing 16 that spans 90 degrees. The aperture 30 defines an end of a channel 32 through which the ultrasonic signal 18, and typically the water, pass. The channel 32 allow the transducer 12 and the water source 14 to be in communication with the aperture 30 to provide for the passage of the ultrasonic signal 18 and water through the housing 16. For the aperture 30 to open toward the component 20, the aperture must be contacting or be near the component such that the ultrasonic signal 18 is sufficiently transmitted to and reflected back from the portion of the component being inspected. The ultrasonic signal 18 is sufficiently transmitted if the signal received by the ultrasonic transducer 12 is able to indicate defects and lack of defects in the inspected component 20. The data acquired from the returning or echoed ultrasonic signal 18 that is received by the ultrasonic transducer 12 is typically processed by a processing element, and the processed data may be presented to a technician via a display. The display may be a cathode ray tube device illustrating an image such as a wave or a contour. Alternatively, the display may be an LED indicator illustrating numerical values or may be any other device to illustrate the processed data. The technician may observe an amount of processed data on the display during the inspection to find internal defects in the component 20 so that the technician can mark or otherwise record the location of the defect for subsequent testing, repair, and/or replacement. Alternatively, the data may be stored for subsequent processing and analysis.

FIG. 3 illustrates the path of the ultrasonic signal 18 through the channel 32. The transducer 12 is in communication with the housing 16 and is preferably threaded into the housing, such that the transducer generally does not move relative to the housing. The transducer 12 may be oriented at any position relative to the housing 16, such as the angled orientation of the transducer illustrated in FIG. 2. The transducer 12 must be attached such that the transmitted and received ultrasonic signal 18 reflects off a reflector, such as the fixed reflector 34 and/or the rotating reflector 36. In the illustrated embodiment, the ultrasonic signal 18 is sent from the ultrasonic transducer 12 and reflects off the fixed reflector 34 and then reflects from the rotating reflector 36 out the aperture 30 toward a portion of the component 20. The fixed reflector 34 and the rotating reflector 36 are in communication with the channel 32. The ultrasonic signal 18 is coupled to the component 20 and propogates therethrough with some portion of the ultrasonic signal reflecting from defects within the component back to the inspection device for reception by the ultrasonic transducer 12. The reflected ultrasonic signal 18 travels back to the transducer 12 and is received by the transducer in a reverse order from which it was sent. Alternatively, the transmitted ultrasonic signal 118 may first reflect off the rotating reflector 136 and then the fixed reflector 134, as illustrated in FIGS. 6 and 7. In addition, three or more reflectors may be included, or only the rotating reflector 36 may be included in further embodiments of the present invention.

The reflectors 34 and 36 of the illustrated inspection device 10 perpendicularly reflect the ultrasonic signal 18. The fixed reflector 34 and the rotating reflector 36 of one embodiment each comprise a rod of stainless steel with a polished 45 degree bevel that functions as an ultrasonic mirror. Further embodiments of the present invention may include ultrasonic mirrors of various materials, shapes, or angles. Still further embodiments of the reflectors 34 and 36 may reflect the ultrasonic signal 18 at any non-perpendicular angle.

FIG. 5 illustrates the assembly of the inspection device 10, wherein each rod is inserted into the housing 16 through holes in the exterior of the housing and retained by retention elements, such as threaded screws 44 and 46. It should be appreciated that the retention element 44 of the rotating reflector 36 prevents or minimizes axial motion of the rod of the rotating reflector while permitting rotational motion of the rotating reflector. Alternative embodiments of the present invention may attach the reflectors 34 and 36 by different means. Set screws 48 and 50 are also preferably used to retain the transducer 12 and seal the channel 32, respectively, although the transducer may be retained and the channel may be sealed in other manners if desired. The water source 14 is preferably threaded into the housing 16, and the transducer 12 may also be threaded into the housing; however, the transducer and water source may be attached to the housing by additional means in alternative embodiments of the present invention.

A handle 38 is provided by the inspection device 10 of one embodiment to rotate the rotating reflector 36. The handle 38 is positioned outside the housing 16 for convenient manipulation by a technician. The handle 38 of FIG. 5 is located on an end of the rotating reflector 36 opposite the polished, beveled end. Alternatively, the handle 38 may be attached to the rod of the rotating reflector 36 such that the two are rotatably fixed. The handle 38 includes a radially-extending protrusion, which in the illustrated embodiment is a cylindrical shaft. Handles of alternative embodiments may include any protrusion or surface texture sufficient for a technician to turn the handle. In addition, the surface of the housing 16 surrounding the handle 38 may include indicators of the preset angle that the handle and rotating reflector 36 may be positioned.

The area of the component 20 that will be inspected is governed by the position of the rotating reflector 36. The rotating reflector 36 causes the ultrasonic signal 18 to be reflected through the aperture 30 of the housing 16 at the various preset angles of the rotating reflector. The rotating reflector 36 is able to rotate along an arc of a specific angular distance, such as the 90 degree arc of the illustrated inspection device 10. Alternative embodiments of the inspection device 10 may have a rotating reflector that can rotate up to, and including, 360 degrees. Accordingly, the ultrasonic signal 18 can be transmitted at any angle along the arc that the rotating reflector 36 is able to rotate.

The inspection device 10 of the present invention permits the ultrasonic signals to be introduced into the component under inspection at two or more different angles without having to reposition the housing 16. For example, the inspection device 10 may define a plurality of preset angles that include two or more preset angles of the rotating reflector 36 that permit an entire radius or surface of a component to be inspected. In this embodiment, the plurality of preset angles are determined prior to the assembly of the inspection device 10 and are based on the minimum number of angular positions required to fully inspect a component 20. The inspection device 10 of FIG. 1, is preferably able to inspect the entire radius of the joint 22 at five preset angles separated by 22.5 degrees; the angles being 0 degrees, 22.5 degrees, 45 degrees, 67.5 degrees, and 90 degrees. Alternative embodiments can inspect a joint 22 or a component 20 using any number of preset angles, non-limiting examples include three angles separated by 45 degrees (0 degrees, 45 degrees, and 90 degrees) or four angles separated by 30 degrees (0 degrees, 30 degrees, 60 degrees, and 90 degrees). Additional embodiments may not inspect at the extremes of 0 degrees and 90 degrees, but may inspect the joint 22 at four preset angles separated by 22.5 degrees; the angles being 11.25 degrees, 33.75 degrees, 56.25 degrees, and 78.75 degrees. Alternatively, the inspection device 10 may include preset angles that are not equally separated.

The ultrasonic signal 18 of a stationary inspection device 10 is able to inspect only a first portion of a component 20 along a single arc unless the ultrasonic signal 18 is moved in a lengthwise direction beyond that first portion of the component. An individual portion of the first portion corresponds to the area of the component 20 that can be inspected by the stationary inspection device 10 at a single preset angle. To inspect portions of second portion, the ultrasonic inspection device 10 must be moved in a lengthwise direction relative to the component 20 to inspect the second and any additional portions of the component. Alternatively, multiple iterations of advancing the device 10 along the joint may inspect lengthwise portions of the component 20 at each of the preset angles. Because different ultrasonic transducers 12 are able to inspect portions of different dimensions, the number of individual portions in a first portion of a component 20, or the number of lengthwise portions defined by the component, depends upon the performance of the ultrasonic transducer.

One method of inspecting a component 20 includes the positioning of the inspection device 10 proximate the component such that the aperture 30 opens toward the component. The rotating reflector 36 is locked at a preset angle so that transmitted ultrasonic signals 18 reflect from the rotating reflector toward a portion of the component. After the individual portion has been inspected, the rotating reflector 36 is moved to another preset angle, preferably by the technician rotating the handle 38, to facilitate inspection of another portion of the component 20. After that portion has been inspected, the rotating reflector 36 is moved to a third preset angle and the inspection signal 18 is transmitted and received to inspect yet another portion. The rotating reflector 36 may be moved, preferably by rotating the handle 38, to a plurality of preset angles and an ultrasonic signal 18 transmitted while the handle is at each preset angle to inspect a first portion of the component 20. The first portion of the component 20 comprises all the individual portions inspected by a stationary inspection device 10 at each preset angle. To inspect a second portion of the component 20, the inspection device 10 is advanced in a lengthwise direction along the component so that the aperture 30 opens toward the second portion. By sequentially rotating the handle 38 to the plurality of preset angles while repeating the transmission of ultrasonic signals 18, all the individual portions of the second portion of the component 20 are inspected. This process of advancing the ultrasonic inspection device 10 and transmitting ultrasonic signals 18 at each preset angle may be further repeated to inspect every individual portion of the component 20 under inspection.

An alternative method of inspecting a component 20 includes advancing the inspection device 10 along the length of the component when the rotating reflector 36 remains locked at a preset angle. This method preferably inspects a lengthwise portion of the component 20. The rotating reflector 36 is then moved to another preset angle and again advanced along the length of the component 20 to inspect a second lengthwise portion of the component. This procedure may be repeated for the remaining preset angles to inspect all the lengthwise portions of the component 20. Further methods of inspecting the component 20 are included in the present invention. As discussed above, one limitation of the inspection device of the '476 patent is the inability of a technician to precisely determine the intermediate angles between the 0 degree and 90 degree positions. The preset angles of the present invention allow a technician to repeatably inspect the intermediate angles between the 0 degree and 90 degree positions. Furthermore, the preset angles eliminate the need to "sweep" the handle as the inspection device 10 is advanced along the component 20, thus the present invention produces more reliable results.

The preset angles are located on the inspection device 10 by a locking mechanism. The locking mechanism of the illustrated embodiment includes at least one detent 40 defined by the rod of the rotating reflector 36 in combination with a spring-loaded ball 42 in the housing 16. The detents 40 are structured to selectively receive the spring-loaded ball 42 to rotatably lock the rotating reflector 36. Preferably, the detents 40 are located on the rotating reflector 36, as shown in FIG. 2. The spring-loaded ball 42 is radially positioned proximate the detents 40 such that the spring-loaded ball is able to partially enter each individual detent to rotatably lock the rotating reflector 36. A rotatably-locked rotating reflector 36 is rotated, and thus rotatably-unlocked, when an amount of torque necessary to push the spring-loaded ball 42 out of the detent 40 is provided, preferably through the handle 38. In an alternative embodiment, the detents 40 are defined in the handle 38 to selectively receive the spring-loaded ball 42 to rotatably lock the handle and the rotating reflector 36 at a preset angle. The detents 40 may be machined or cast in the rotating reflector 36 or handle 38. The detents 40 are angularly positioned to correspond with the preset angles of the inspection device 10. Further embodiments of the present invention may include other locking mechanisms that rotatably lock the rotating reflector 36 at preset angles. In addition, the locking mechanism of alternative embodiments of the present invention may allow the preset angles to be adjusted such that any desired angle may define a preset angle FIG. 4 illustrates an inspection using two alternative sets of preset angles. The preset angles on the left side of the T-joint of the component 22 are separated by an angle $\alpha$, which is 22.5 degrees. The preset angles on the right side of the T-joint of the component 22 are separated by an angle $\beta$, which is 30 degrees. The required angular separation between the present angles is governed by the ultrasonic transducer 12 used in the inspection device 10 because of the dimensions of a portion the transducer can inspect when the inspection device is stationary. To manufacture the inspection device 10, the minimum number of preset angles required for a particular ultrasonic transducer 12 to substantially inspect a joint 22 or a component 20 is determined, then the angular separations of the preset angles are calculated to specify the locations of the detents 40 in the rotating reflector 36 or handle 38. The inspection device 10 may also be calibrated using the preset angles to ensure more accurate results. Accordingly, the efficiency of the inspection device 10 is improved by inspecting the maximum area of the component 20 with the minimum number of iterations.

Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An ultrasonic inspection device, comprising:
   a housing defining a channel for the passage of an ultrasonic signal;
   a transducer in communication with the housing for transmitting and receiving the ultrasonic signal therethrough;
   a rotating reflector in communication with the channel to reflect the ultrasonic signal at two or more preset angles; and
   a locking mechanism to lock the rotating reflector at the preset angles, wherein the locking mechanism comprises a spring-loaded ball and detent assembly.

2. An ultrasonic inspection device according to claim 1, further comprising a fixed reflector in communication with the channel for reflecting the ultrasonic signal.

3. An ultrasonic inspection device according to claim 2 wherein the fixed reflector directly reflects the ultrasonic signal to and from the transducer.

4. An ultrasonic inspection device according to claim 2 wherein the rotating reflector directly reflects the ultrasonic signal to and from the transducer.

5. An ultrasonic inspection device according to claim 2 wherein the fixed reflector comprises a rod with a polished 45 degree bevel and the rotating reflector comprises a rod with a polished 45 degree bevel.

6. An ultrasonic inspection device according to claim 1, further comprising a handle attached to the rotating reflector for rotation of the rotating reflector.

7. An ultrasonic inspection device according to claim 6 wherein the spring-loaded ball and detent assembly comprises a spring-loaded ball in the housing and at least one detent defined by the handle for selectively receiving the spring-loaded ball to rotatably lock the rotating reflector, wherein at least one detent of the spring-loaded ball and detent assembly corresponds with the preset angles.

8. An ultrasonic inspection device according to claim 1 wherein the spring-loaded ball and detent assembly comprises a spring-loaded ball in the housing and at least one detent defined by the rotating reflector for selectively receiving the spring-loaded ball to rotatably lock the rotating reflector, wherein at least one detent of the spring-loaded ball and detent assembly corresponds with the preset angles.

9. An ultrasonic inspection device according to claim 1 wherein the housing defines an aperture for the passage of the ultrasonic signal.

10. An ultrasonic inspection device according to claim 9 wherein the aperture is arcuate and spans at least 90 degrees.

11. An ultrasonic inspection device, comprising:
a housing having a channel for the passage of an ultrasonic signal;
a transducer in communication with the housing for transmitting and receiving the ultrasonic signal therethrough;
a fixed reflector in communication with the channel to reflect the ultrasonic signal;
a rotating reflector in communication with the channel to reflect the ultrasonic signal at a plurality of preset angles;
a handle attached to the rotating reflector for rotation of the rotating reflector; and
a locking mechanism to lock the rotating reflector at the preset angles, wherein the locking mechanism comprises a spring-loaded ball and detent assembly.

12. An ultrasonic inspection device according to claim 11 wherein the fixed reflector comprises a rod with a polished 45 degree bevel and the rotating reflector comprises a rod with a polished 45 degree bevel.

13. An ultrasonic inspection device according to claim 11 wherein the spring-loaded ball and detent assembly comprises a spring-loaded ball in the housing and at least one detent defined by the handle for selectively receiving the spring-loaded ball to rotatably lock the rotating reflector, wherein at least one detent of the spring-loaded ball and detent assembly corresponds with the preset angles.

14. An ultrasonic inspection device according to claim 11 wherein the spring-loaded ball and detent assembly comprises a spring-loaded ball in the housing and at least one detent defined by the rotating reflector for selectively receiving the spring-loaded ball to rotatably lock the rotating reflector, wherein at least one detent of the spring-loaded ball and detent assembly corresponds with the preset angles.

15. An ultrasonic inspection device according to claim 11 wherein the housing defines an aperture for the passage of the ultrasonic signal.

16. An ultrasonic inspection device according to claim 15 wherein the aperture is arcuate and spans at least 90 degrees.

17. A method of inspecting a component, comprising the steps of:

positioning an ultrasonic inspection device proximate the component to be inspected such that an aperture defined by the ultrasonic inspection device opens toward the component;
utilizing a spring-loaded ball and detent assembly to lock a rotating reflector at a preset angle;
transmitting an ultrasonic signal through the ultrasonic inspection device such that the ultrasonic signal reflects from the rotating reflector toward a portion of the component;
moving the rotating reflector to another preset angle to facilitate inspection of another portion of the component; and
transmitting additional ultrasonic signals through the ultrasonic inspection device such that the ultrasonic signal reflects from the rotating reflector toward an additional portion of the component.

18. A method according to claim 17 wherein moving the rotating reflector comprises rotating a handle that is rotatably attached to the rotating reflector prior to transmitting additional ultrasonic signals.

19. A method according to claim 18 wherein moving the rotating reflector comprises rotating the handle to a third preset angle prior to transmitting additional ultrasonic signals.

20. A method according to claim 19 wherein moving the rotating reflector comprises:
rotating the handle to a plurality of preset angles and transmitting additional ultrasonic signals with the handle at each preset angle to inspect a first portion of the component; and
advancing the ultrasonic inspection device along the length of the component to a second portion of the component following the inspection of the first portion of the component and repeating the transmission of ultrasonic signals with the handle sequentially rotated to the plurality of preset angles to inspect the second portion of the component.

21. A method according to claim 17, further comprising the step of advancing the ultrasonic inspection device along the length of the component while the rotating reflector remains locked at the preset angle and the ultrasonic signals are transmitted so as to inspect a lengthwise portion of the component at the preset angle prior to moving the rotating reflector to another preset angle.

22. A method according to claim 21, further comprising the step of again advancing the ultrasonic inspection device along the length of the component after moving the rotating reflector to another preset angle to inspect further portions of the component along the length of the component at the other preset angle.

* * * * *